US008131488B2

(12) United States Patent
Kagawa

(10) Patent No.: US 8,131,488 B2
(45) Date of Patent: Mar. 6, 2012

(54) BATTERY MANAGEMENT SYSTEM AND CHARGER

(75) Inventor: Ryohei Kagawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/789,753

(22) Filed: May 28, 2010

(65) Prior Publication Data

US 2010/0241377 A1 Sep. 23, 2010

Related U.S. Application Data

(63) Continuation of application No. PCT/JP2007/072945, filed on Nov. 28, 2007.

(51) Int. Cl.
*G01R 31/36* (2006.01)
(52) U.S. Cl. .......................................................... 702/63
(58) Field of Classification Search ..................... 702/63
See application file for complete search history.

(56) References Cited

U.S. PATENT DOCUMENTS

| 5,654,623 | A | * | 8/1997 | Shiga et al. ................... 320/106 |
| 5,694,019 | A | | 12/1997 | Uchida et al. |
| 7,443,135 | B2 | * | 10/2008 | Cho .............................. 320/108 |
| 2002/0156537 | A1 | | 10/2002 | Sakakibara et al. |
| 2003/0169019 | A1 | | 9/2003 | Oosaki |
| 2004/0039534 | A1 | | 2/2004 | Trembley |
| 2004/0196006 | A1 | | 10/2004 | Kawaguchi et al. |
| 2007/0244471 | A1 | * | 10/2007 | Malackowski ..................... 606/1 |
| 2008/0071483 | A1 | * | 3/2008 | Eaves .............................. 702/63 |

FOREIGN PATENT DOCUMENTS

| JP | 05-172914 | 7/1993 |
| JP | 09-153376 | 6/1997 |
| JP | 10-066266 | 3/1998 |
| JP | 2002-313433 | 10/2002 |
| JP | 2003-007348 | 1/2003 |
| JP | 2003-256084 | 9/2003 |
| JP | 2006-172884 | 6/2006 |
| JP | 2007-87707 | 4/2007 |

OTHER PUBLICATIONS

Extended European Search Report dated Mar. 29, 2011.
International Search Report dated Jan. 29, 2008.
Japanese Official Action dated Jul. 6, 2010 together with an English language translation.

* cited by examiner

*Primary Examiner* — Cindy H Khuu
(74) *Attorney, Agent, or Firm* — Scully, Scott, Murphy & Presser, P.C.

(57) ABSTRACT

A battery management system includes a battery attached with an identification ID; and a plurality of chargers for reading the identification ID attached to the battery, the chargers associating the read identification ID with information indicative of an end of charging the battery and sending the information, the chargers charging the battery. The battery management system also includes a management server connected to each of the chargers for receiving the information indicative of the end of charging the battery associated with the identification ID and sent from each of the chargers. The management server cumulatively sums, as the number of chargings, the number of receptions of the information indicative of the end of charging the battery for each identification ID, and the management server associates the identification ID with the cumulatively summed number of chargings and allows the number of chargings to be recorded.

4 Claims, 9 Drawing Sheets

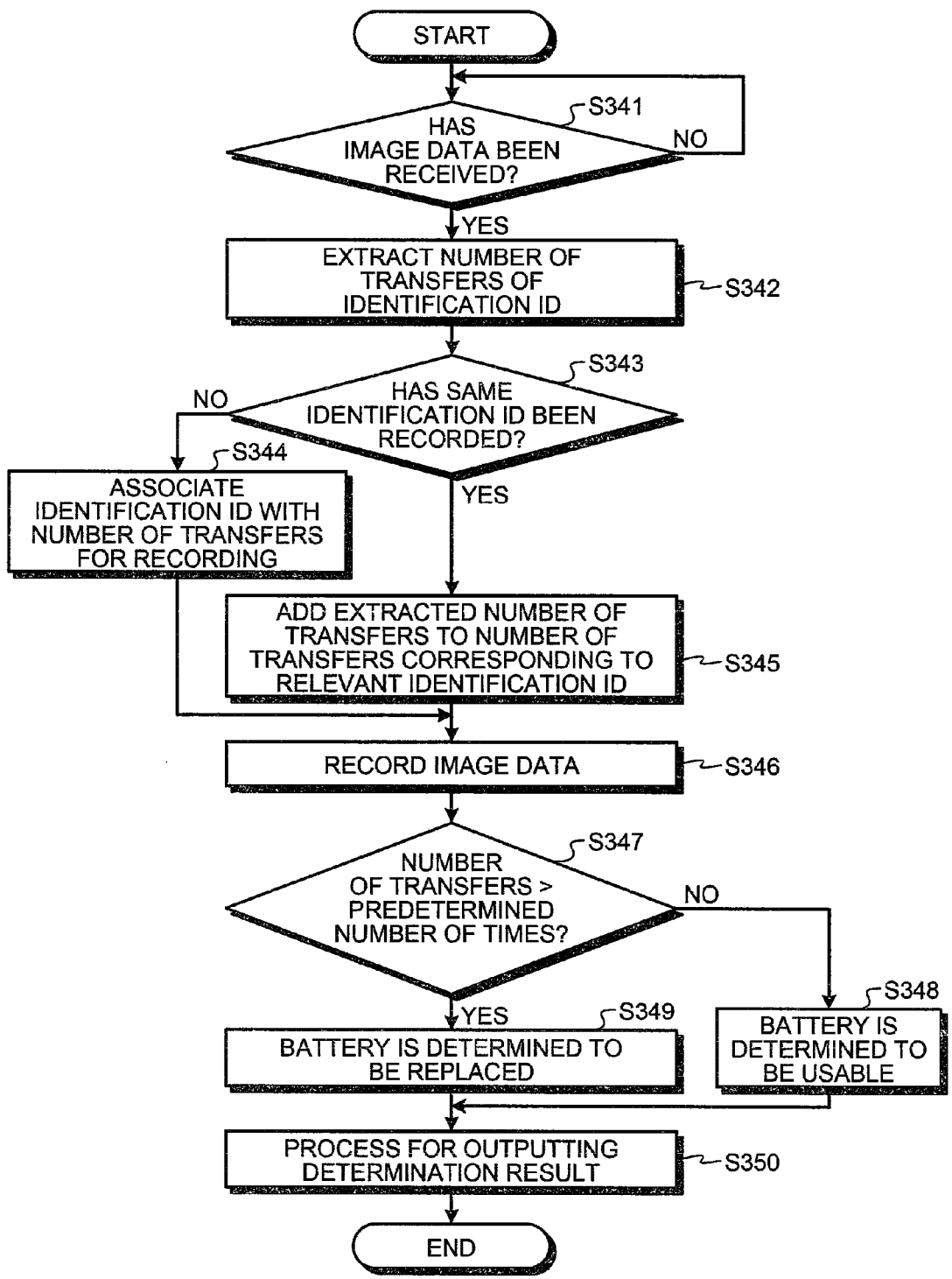

BATTERY MANAGEMENT SYSTEM AND CHARGER

CROSS-REFERENCE TO RELATED APPLICATIONS

This application is a continuation of PCT international application Ser. No. PCT/JP2007/072945 filed on Nov. 28, 2007 which designates the United States, incorporated herein by reference, incorporated herein by reference.

BACKGROUND OF THE INVENTION

1. Field of the Invention

The present invention relates to a battery management system and a charger for managing the charging and service life of batteries to which an identification ID is attached.

2. Description of the Related Art

Conventionally, some chargers were designed to allow the reading device to read out the identifier for identifying a battery, so that the number of chargings was updated and stored for each battery (see Japanese Laid-open Patent Publication No. 05-172914). On the other hand, as for battery management methods, some of them were designed in a manner such that chargers were given a function of reading identification information provided to batteries in use and one of the chargers connected to a computer was given a function of sending identification information and charging voltage information to the computer in order to manage the information of individual batteries by the computer (see Japanese Laid-open Patent Publication No. 10-66266). In another battery management method, each charging device was configured to send the identifier of a battery to the computer upon charging the battery (see Japanese Laid-open Patent Publication No. 2002-313433).

SUMMARY OF THE INVENTION

A battery management system according to an aspect of the present invention includes a battery attached with an identification ID; a plurality of chargers for reading the identification ID attached to the battery, the chargers associating the read identification ID with information indicative of an end of charging the battery and sending the information, the chargers charging the battery; and a management server connected to each of the chargers for receiving the information indicative of the end of charging the battery associated with the identification ID and sent from each of the chargers, the management server cumulatively summing, as the number of chargings, the number of receptions of the information indicative of the end of charging the battery for each identification ID, the management server associating the identification ID with the cumulatively summed number of chargings and allowing the number of chargings to be recorded, the management server managing battery service life based on the number of chargings.

A battery management system according to another aspect of the present invention includes a battery attached with an identification ID; a plurality of chargers for reading the identification ID attached to the battery and associating the read identification ID with the number of chargings of the battery for storage, the chargers associating an identification ID with the recorded number of chargings of the battery and sending the number of chargings, the chargers erasing the recording of the sent number of chargings of the battery and charging the battery; and a management server connected to each of the chargers for receiving the number of chargings of the battery associated with the identification ID and sent from each of the chargers, the management server cumulatively summing the number of chargings of the battery for each identification ID, the management server associating the identification ID with the cumulatively summed number of chargings and allowing the number of chargings to be recorded, the management server managing battery service life based on the number of chargings.

A battery management system according to still another aspect of the present invention includes a processing device for reading an identification ID attached to a loaded battery, the processing device associating the read identification ID with the number of chargings of the battery and allowing the number of chargings to be recorded, the processing device performing predetermined processing; a plurality of chargers for associating the identification ID with the number of chargings of the battery recorded in the processing device and sending the number of the chargings, the chargers erasing the recording of the sent number of chargings of the battery and charging the battery; and a management server connected to each of the chargers for receiving information regarding the number of chargings of the battery associated with the identification ID and sent from each of the chargers, the management server cumulatively summing the received number of chargings of the battery for each identification ID, the management server associating the identification ID with the cumulatively summed number of chargings and allowing the number of chargings to be recorded, the management server managing battery service life based on the recorded number of chargings.

A charger according to still another aspect of the present invention constitutes a battery management system in conjunction with another charger and a management server, and sends information for centralized management of service life of a battery to the management server and charging the battery. The charger includes a readout unit for reading an identification ID attached to the battery; and a sending unit for associating the read identification ID with the information indicative of an end of charging the battery and sending the information as the information for centralized management of the service life of the battery.

A charger according to still another aspect of the present invention constitutes a battery management system in conjunction with another charger and a management server, and sends information for centralized management of service life of a battery to the management server and charging the battery. The charger includes a readout unit for reading the identification ID attached to the battery; a recording unit for associating the read identification ID with the number of chargings of the battery and allowing the number of chargings to be recorded as information for centralized management of the service life of the battery; a sending unit for associating the number of chargings of the battery recorded in the recording unit with the identification ID and sending the number of chargings; and an erase unit for erasing from the recording unit the recorded number of chargings of the battery sent by the sending unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is an explanatory flowchart for the control operation of a management server shown in FIG. 6.

DETAILED DESCRIPTION OF THE PREFERRED EMBODIMENTS

Battery management systems and chargers according to embodiments of the present invention will be described in detail with reference to FIGS. 1 to 9. Note that the present invention is not limited to these embodiments but may be modified in a variety of ways without departing from the scope of the present invention.

First Embodiment

Figure 1:
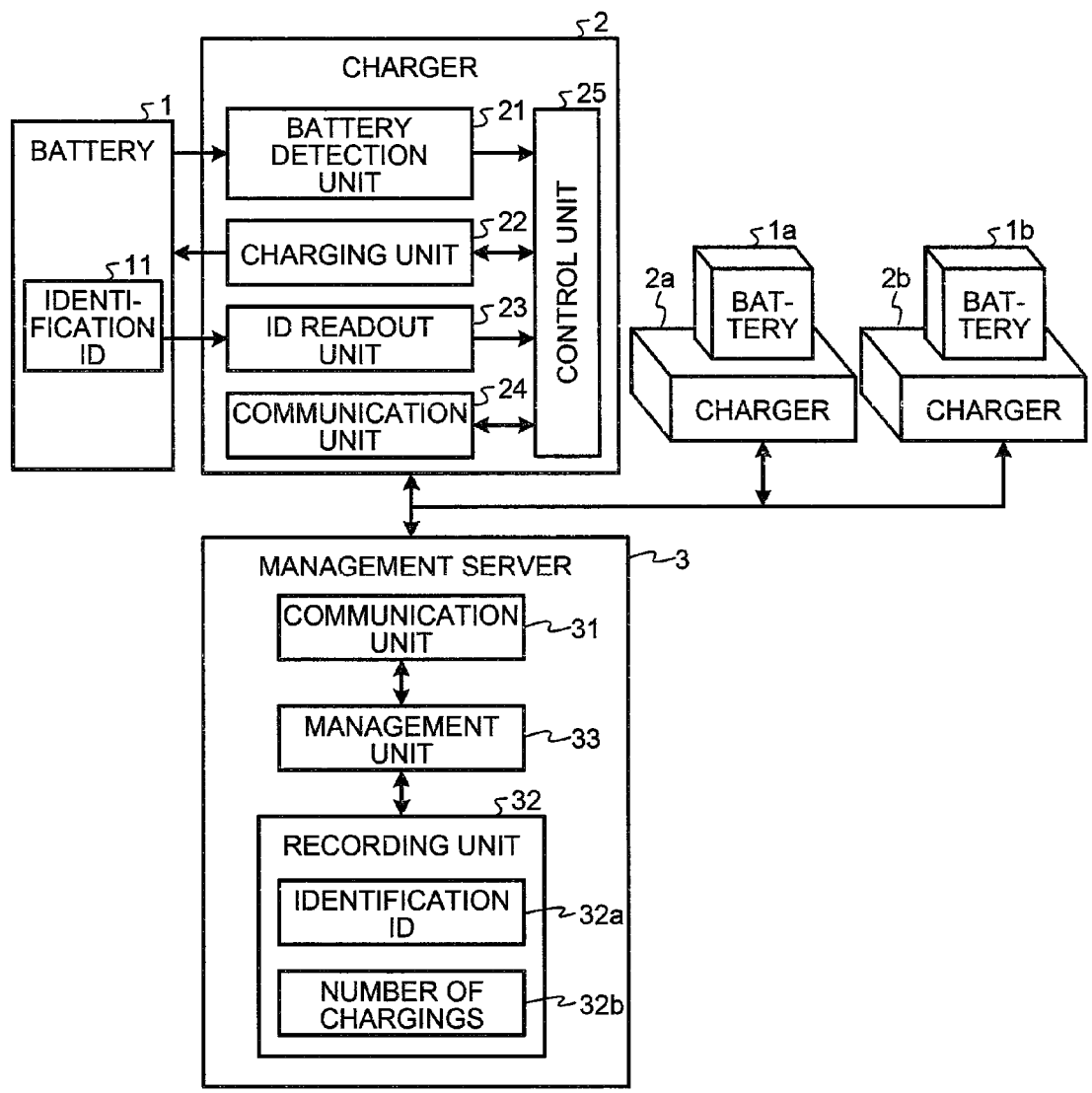
FIG. 1 is a system block diagram illustrating the configuration of a battery management system according to a first embodiment of the present invention.

FIG. 1 is a system block diagram illustrating the configuration of a battery management system according to a first embodiment of the present invention. In FIG. 1, the battery management system has a plurality of batteries 1, 1a, and 1b, a plurality of chargers 2, 2a, and 2b, and a management server 3.

The batteries 1, 1a, and 1b include a rechargeable battery which can be recharged by chargers, and for example, loaded in a processing device such as an information terminal device. This battery has an identification ID such as a barcode fixedly attached thereto in a readable manner. Note that the identification ID may also be an RF ID tag.

The chargers 2, 2a, and 2b are configured to charge the batteries 1, 1a, and 1b mounted. These chargers are all configured in the same manner, and thus a description will be made typically to the configuration of the charger 2. The charger 2 includes a battery detection unit 21, a charging unit 22, an ID readout unit 23, a communication unit 24, and a control unit 25 for controlling each of these units.

The battery detection unit 21 is configured to detect the battery 1 when it is mounted or dismounted. For example, the battery detection unit 21 detects the battery 1 mounted on the charger 2 for a certain period of time and inform the control unit 25 of it.

The charging unit 22 charges the battery 1 by supplying DC electricity thereto under the control of the control unit 25. The control unit 25 allows the charging unit 22 to measure the voltage and resistance of the battery 1 in order to determine whether the battery 1 satisfies the predetermined requirements necessary for charging. If the battery 1 is determined to have satisfied the predetermined requirements, the control unit 25 ends the charging of the battery 1.

The ID readout unit 23 has an optical reading function as a readout unit. Under the control of the control unit 25 and based on a beam of light reflected from an identification ID 11 such as a barcode or an optical information storage medium, the ID readout unit 23 reads the information of the barcode and then delivers the read information to the control unit 25. Note that when the identification ID 11 is an RF ID tag, then the ID readout unit 23 is a reader/writer for reading and writing the information of the RF ID tag. The control unit 25 recognizes the identification ID 11 based on the information from the ID readout unit 23.

The communication unit 24 has a function as a sending unit. Under the control of the control unit 25, the communication unit 24 associates the information indicative of the end of charging the battery 1 with the identification ID 11 of the battery 1 read by the ID readout unit 23 and sends the information to the management server 3. The control unit 25 may control the communication unit 24 to send the information indicative of the end of charging a battery upon completing the charging of the battery. Alternatively, the control unit 25 may also control the communication unit 24 to send the information indicative of the end of charging a battery in response to the request for polling from the management server 3. Furthermore, the control unit 25 is operated to charge the battery 1 mounted to the charger 2, and then end the charging when the battery 1 has satisfied the predetermined requirements necessary for charging.

The management server 3 is electrically connected to a plurality of chargers 2, 2a, and 2b, for example, via a network. The management server 3 includes a communication unit 31, a recording unit 32, and a management unit 33 for controlling each of these units.

Under the control of the management unit 33, the communication unit 31 receives the information indicative of the end of charging a battery associated with the identification ID and sent from each of the chargers 2, 2a, and 2b and sends the information to the management unit 33. Upon input of the information indicative of the end of charging a battery, the management unit 33 cumulatively sums, as the number of chargings, the number of receptions of the information indicative of the end of charging the battery for each identification ID, and allows the cumulatively summed number of chargings to be recorded in the recording unit 32. Under the control of the management unit 33, the recording unit 32 associates an identification ID 32a with the cumulatively summed number of chargings 32b for recording. The management unit 33 manages the service life of the battery based on the number of chargings 32b recorded in the recording unit 32. That is, when the predefined given number of chargings has been reached, the management unit 33 assumes that the battery has reached its useful life limit, and then for example, sends a notice such as a message for requesting the replacement of the battery.

Figure 2:
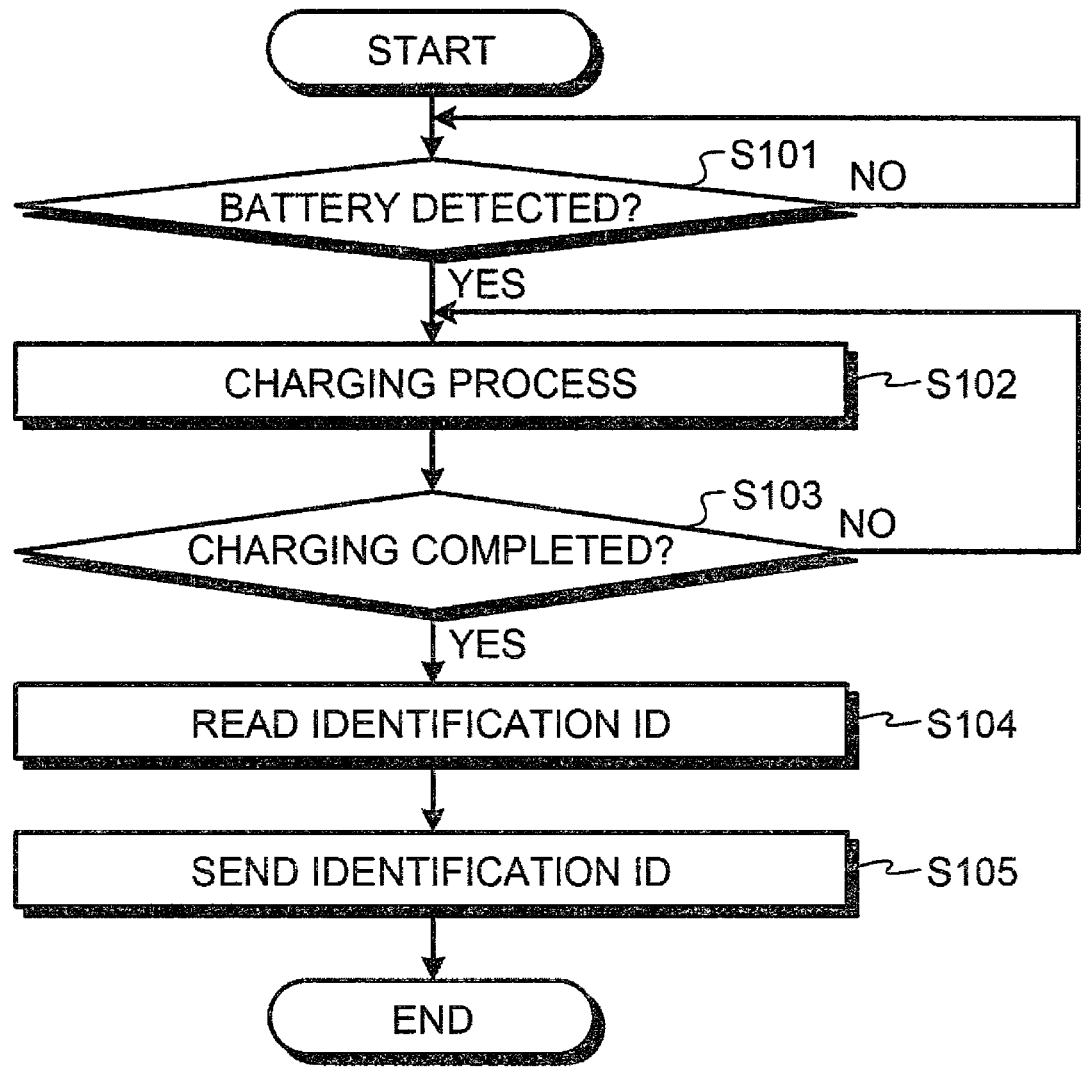
FIG. 2 is an explanatory flowchart for the control operation of a charger shown in FIG. 1.

A description will now be made to the control operation of the charger 2 and the management server 3 with reference to the flowcharts of FIGS. 2 and 3. FIG. 2 is an explanatory flowchart for the control operation of the charger 2 shown in FIG. 1. In FIG. 2, first, when the battery 1 is mounted on the charger 2 and the battery detection unit 21 has detected the battery 1 (for Yes in step S101), the control unit 25 of the charger 2 charges the battery 1 via the charging unit 22 (step S102). Note that when the battery detection unit 21 has not detected the battery 1 (for No in step S101), the control unit 25 repeats step S101.

Subsequently, the control unit 25 determines whether the battery 1 has satisfied the predetermined requirements necessary for charging, thereby determining the end of the charging (step S103). When the battery 1 has satisfied the predetermined requirements, the control unit 25 determines that the charging has been completed (for Yes in step S103), and then ends the charging. Note that if the process determines in step S103 that the charging has not yet been completed (for No in step S103), then the control unit 25 returns to the aforementioned step S102 to repeat the processing procedures from step S102 onward. Upon completing the charging, the control unit 25 reads the identification ID 11 attached to the battery 1 (step S104), associates the identification ID 11 with the information indicative of the end of charging, and sends it to the management server 3 (step S105). The aforementioned operation is then ended.

Figure 3:
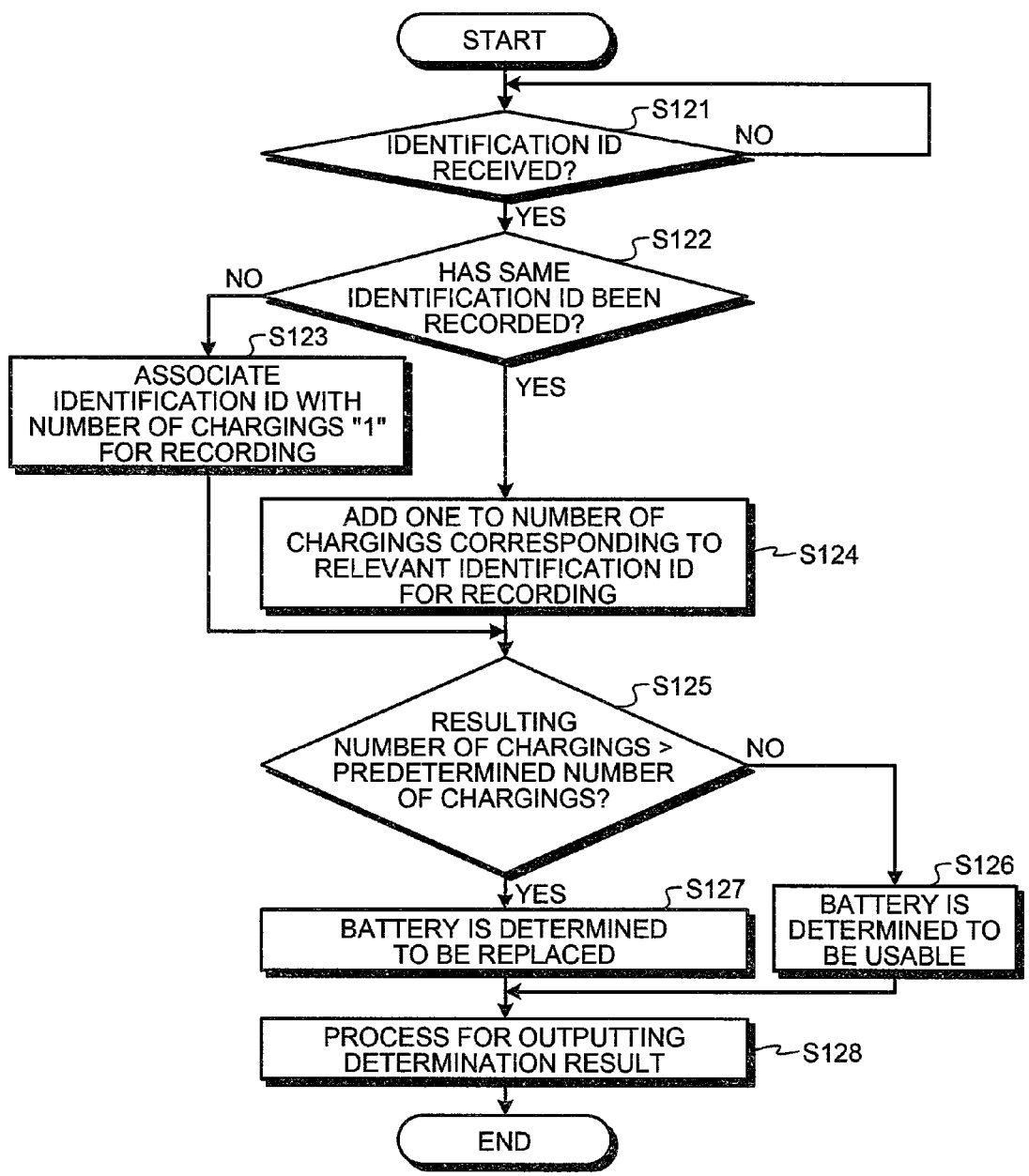
FIG. 3 is an explanatory flowchart for the control operation of a management server shown in FIG. 1.

FIG. 3 is an explanatory flowchart for the control operation of the management server 3 shown in FIG. 1. In FIG. 3, upon reception of the information indicative of the end of charging associated with the identification ID 11 from the charger 2 (for Yes in step S121), the management unit 33 of the management server 3 searches the recording unit 32 to determine whether the same identification ID as the identification ID 11 has been recorded (step S122). Note that if the information on the end of charging has not yet been received (for No in step S121), the management unit 33 repeats step S121.

Here, if the same identification ID has not been recorded in the recording unit 32 (for No in step S122), the management unit 33 assumes, as the number of chargings, the number of receptions of the information indicative of the end of charging the battery 1. Then, the management unit 33 associates the identification ID 11 with the number of chargings "1" and allows it to be recorded in the recording unit 32 (step S123). On the other hand, if the same identification ID has been recorded (for Yes in step S122), the number of receptions of the information indicative of the end of charging the battery 1 is assumed as the number of chargings. Then, the management unit 33 cumulatively adds "1" to the number of chargings corresponding to the relevant identification ID 11 among the identification IDs 32a present in the recording unit 32 and allows it to be recorded in the recording unit 32 (step S124).

Now, the management unit 33 determines whether the number of chargings corresponding to the identification ID 11 has reached the predetermined number of times (step S125). If the number of chargings has not yet reached the predetermined number of times (for No in step S125), the battery 1 is determined to have not yet reached its useful life limit, and is then determined to be in a normal condition and thus usable (step S126). On the other hand, if the number of chargings has reached the predetermined number of times (for Yes in step S125), the battery 1 is determined to have reached its useful life limit and thus determined to be replaced (step S127). After the aforementioned determination has been completely made, the management unit 33 outputs the determination result to the charger 2 (step S128), and then ends the aforementioned control operation.

As such, in the first embodiment, upon reception of the information indicative of the end of charging the battery 1 corresponding to the identification ID from each of the chargers 2, 2a, and 2b, the management server 3 cumulatively sums, as the number of chargings, the number of receptions of this information for each identification ID. Then, the management server 3 associates this cumulatively summed number of chargings with the identification ID and allows it to be recorded in the recording unit 32 as well as manages battery service life based on the number of chargings. This allows the management server to provide simple centralized management of battery service life.

Note that in the first embodiment, the information indicative of the end of charging the battery 1 was to be sent to the management server; however, the present invention is not limited thereto. For example, the battery 1 attached with an identification ID may be loaded in a processing device (not shown) such as an information terminal device for performing predetermined processing. In place of the information indicative of the end of charging the battery 1, the charger 2 can be set to associate the identification ID 11 of the battery 1 with the information indicative of the end of the processing performed by the processing device and to send it. That is, when the amount of battery consumption to be used for one cycle of the processing performed by the processing device is known, the number of times of processing performed by the processing device which has used the battery can be detected, thereby managing battery service life. The management server 3 can be set to receive the information indicative of the end of the aforementioned processing associated with the identification ID and sent from each the chargers 2, 2a, and 2b, to cumulatively sum, as the number of times of processing, the number of receptions of the information indicative of the end of the processing for each identification ID, and to associate the identification ID with this cumulatively summed number of times of processing and allow it to be recorded as well as to manage battery service life based on this number of times of processing. In this case, as with the first embodiment, it is also possible for the management server 3 to provide simple centralized management of service life of batteries.

Second Embodiment

Figure 4:
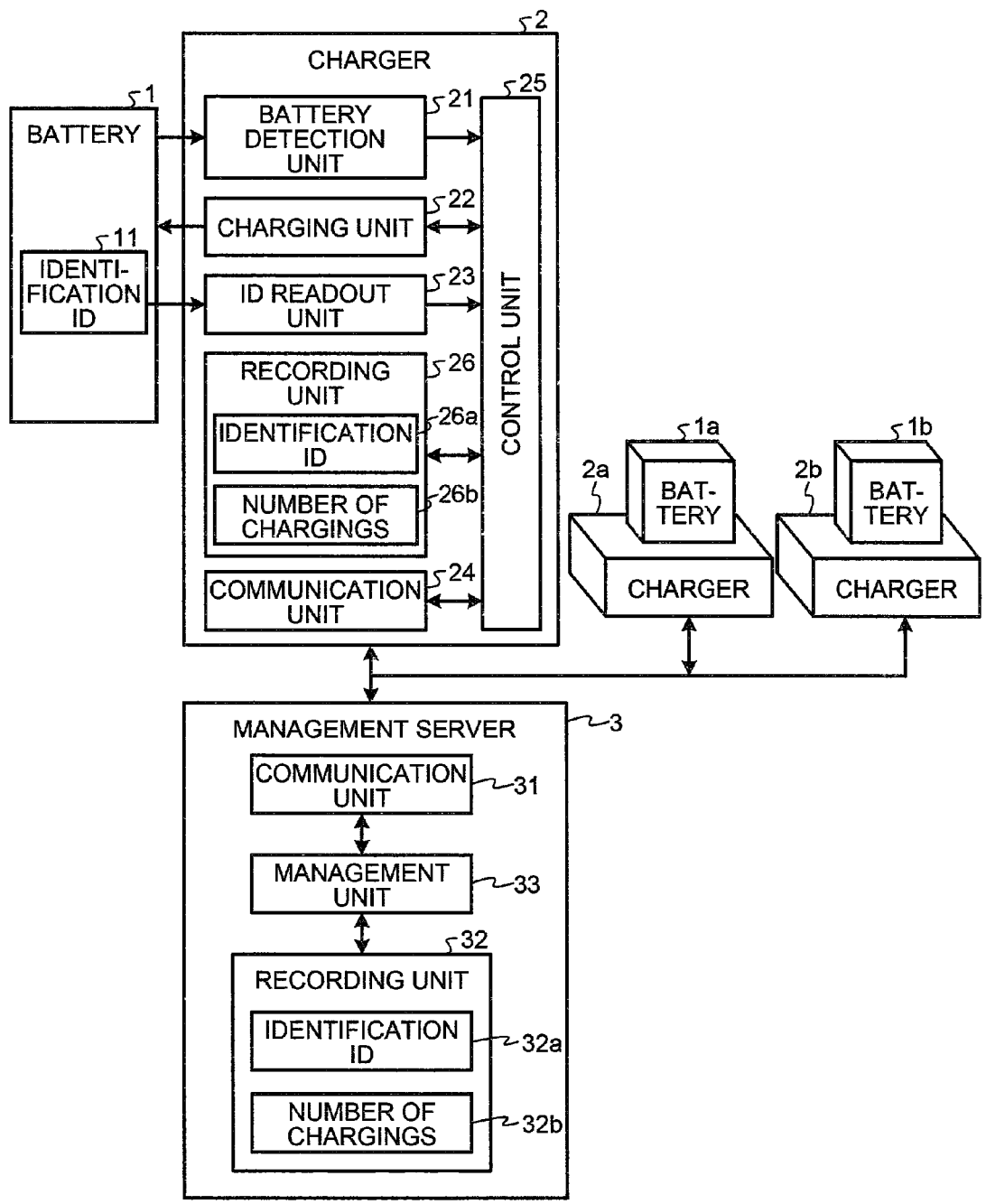
FIG. 4 is a system block diagram illustrating the configuration of a battery management system according to a second embodiment of the present invention.

FIG. 4 is a system block diagram illustrating the configuration of a battery management system according to a second embodiment of the present invention. In FIG. 4, this system is different from the battery management system shown in FIG. 1 in that the charger 2 includes a recording unit 26 in which the number of chargings 26b corresponding to an identification ID 26a is recorded.

For example, when the charger 2 is in such an environment as in the hospital where it is always ready to access to a network, the charger 2 may send the information indicative of the end of charging to the management server 3 each time a battery is charged as in the first embodiment. However, suppose that the charger is allowed to charge a battery outside such an environment (outside the network) for screening inspection or the like. In this case, the charger 2 without the recording unit 26 for recording the number of chargings would not be able to send the information indicative of the number of chargings to the management server 3 when the charger 2 is connected to a network later.

In this context, in the second embodiment, the charger 2 is provided with the recording unit 26 to temporarily record the number of chargings 26b corresponding to each identification ID 26a in the recording unit 26, so that when the charger 2 is connected to a network, the communication unit 24 sends the information regarding the number of chargings 26b to the management server 3. Furthermore, in the second embodiment, the control unit 25 includes an erase unit function for erasing from the recording unit 26 the recording of the number of battery chargings 26b sent by the communication unit 24 so that the number of chargings is sent in a non-overlapping manner to the management server 3.

Figure 5:
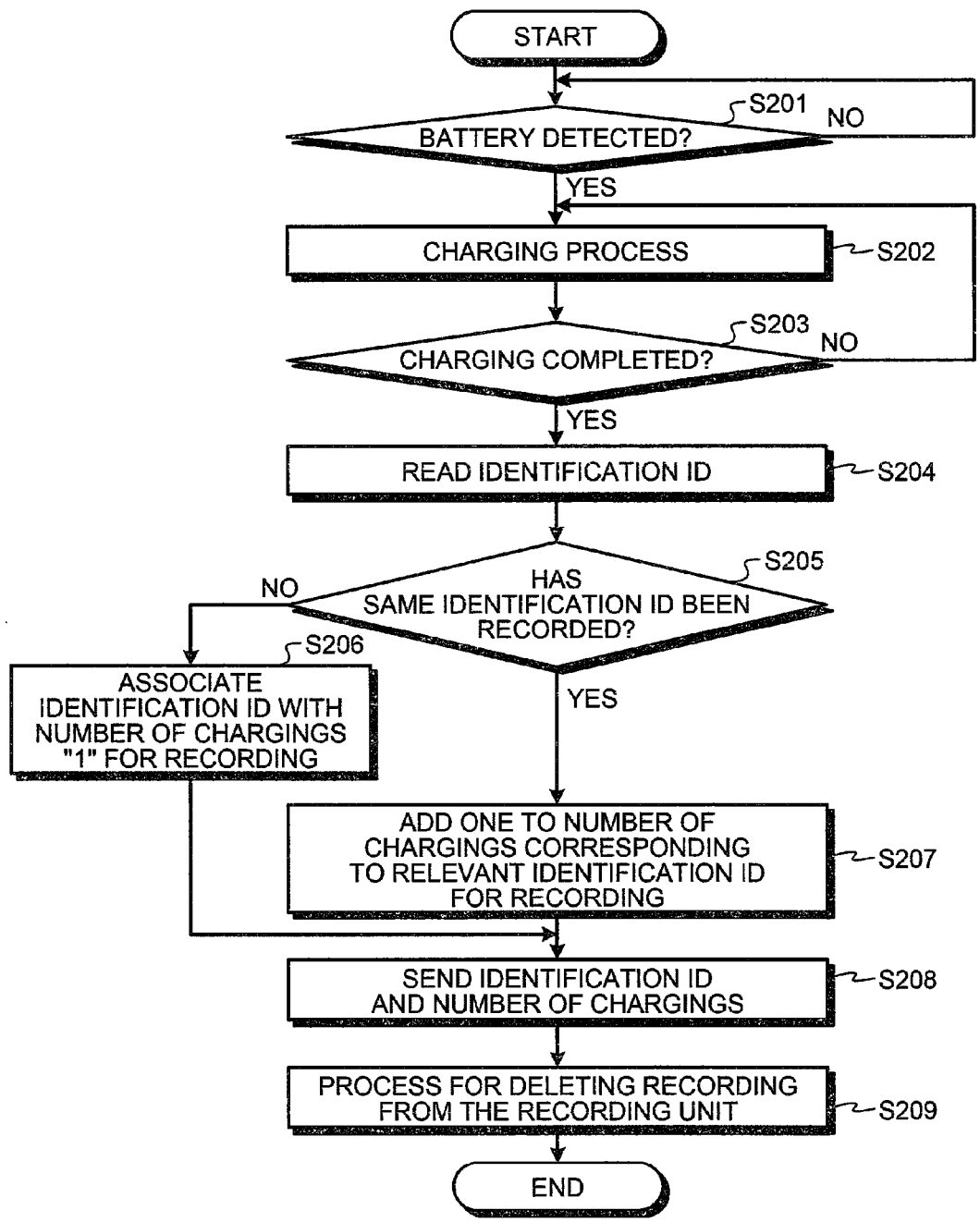
FIG. 5 is an explanatory flowchart for the control operation of a charger shown in FIG. 4.

A description will now be made to the control operation of the charger 2 with reference to the flowchart of FIG. 5. In FIG. 5, first, if the battery 1 is mounted on the charger 2 and detected by the battery detection unit 21 (for Yes in step S201), then the control unit 25 of the charger 2 charges the battery 1 via the charging unit 22 (step S202). Note that if the battery 1 has not been detected by the battery detection unit 21 (for No in step S201), the control unit 25 repeats this step S201.

Now, the control unit 25 determines whether the battery 1 has satisfied the predetermined requirements necessary for charging, thereby determining the end of the charging (step S203). If the battery 1 has satisfied the predetermined requirements, the control unit 25 determines that the charging has been completed (for Yes in step S203), and then ends the charging. Note that if it was determined in step S203 that the charging has not been completed (for No in step S203), the control unit 25 returns to the aforementioned step S202 to repeat the processing procedures of the step S202 onward. Upon completion of the charging, the control unit 25 reads the identification ID 11 attached to the battery 1 (step S204), and then searches the recording unit 26 to determine whether the same identification ID as the identification ID 11 has been recorded (step S205).

At this stage, if the same identification ID has not been recorded in the recording unit 26 (for No in step S205), then the control unit 25 determines that the identification ID should be additionally recorded, allowing the number of chargings "1" to be associated with the identification ID 11 and to be recorded in the recording unit 26 (step S206). On the other hand, if the same identification ID has been recorded in the recording unit 26 (for Yes in step S205), then "1" is cumulatively added to the number of chargings corresponding to the relevant identification ID 11 and recorded in the recording unit 26 (step S207).

Subsequently, the control unit 25 is configured to send the number of chargings associated with this identification ID to the management server 3 (step S208). Furthermore, the control unit 25 erases from the recording unit 26 the recording of the number of chargings associated with the identification ID sent (step S209), and then ends the aforementioned operation.

The management unit 33 of the management server 3 performs the same control operation as that of the first embodiment shown in FIG. 3, and thus can cumulatively sum the number of chargings of the battery 1 for each identification ID. Subsequently, the management unit 33 can associate an identification ID with this cumulatively summed number of chargings and allow it to be recorded it in the recording unit 32. Then, the management unit 33 can determine the service life of the battery based on the recorded number of chargings 32b, thereby managing the service life of each of the batteries 1, 1a, and 1b.

As such, the second embodiment allows each of the chargers 2, 2a, and 2b to associate the number of chargings of the batteries 1, 1a, and 1b with the identification ID to record it, and the management server 3 to receive the number of chargings of the battery corresponding to the identification ID from each of the chargers 2, 2a, and 2b. The management server 3 then cumulatively sums the number of chargings for each identification ID, associates the cumulatively summed number of chargings with the identification ID and allows it to be recorded. Furthermore, the management server 3 manages battery service life based on the number of chargings. This allows the management server to provide simple centralized management of the service life of batteries.

Furthermore, in the second embodiment, each of the chargers 2, 2a, and 2b is provided with the recording unit 26 for recording the number of chargings of the batteries 1, 1a, and 1b. This allows for recording the number of chargings in the recording unit 26 of the charger 2 when the charger charges a battery outside the environment of a network. Thus, when the charger 2 is connected to the network later, the charger 2 can send the number of chargings to the management server 3 and as well provide simple centralized management of the service life of batteries.

Furthermore, the second embodiment allows the charger 2 to erase from the recording unit 26 the recording of the number of battery chargings sent to the management server 3. This allows for preventing overlapped transmissions of the number of chargings to the management server 3 as well as providing simple centralized management of the service life of batteries.

Note that in the second embodiment, as with the first embodiment, the battery 1 attached with the identification ID 11 is loaded in a processing device (not shown) such as an information terminal device for performing predetermined processing. Thus, in place of the information regarding the number of battery chargings, the charger 2 can be set to associate the information indicative of the end of the processing performed by the processing device with the identification ID 11 of the battery 1 and to allow the information to be recorded in the recording unit 26 as well as to send it. The management server 3 can be set to receive the information indicative of the end of the aforementioned processing associated with the identification ID and sent from each of the chargers 2, 2a, and 2b, to cumulatively sum, as the number of times of processing, the number of receptions of the information indicative of the end of the processing for each identification ID, and to associate this cumulatively summed number of times of processing with the identification ID and allow it to be recorded as well as to manage battery service life based on the number of times of processing. In this case, as with the second embodiment, the management server 3 can provide simple centralized management of the service life of batteries.

Third Embodiment

Figure 6:
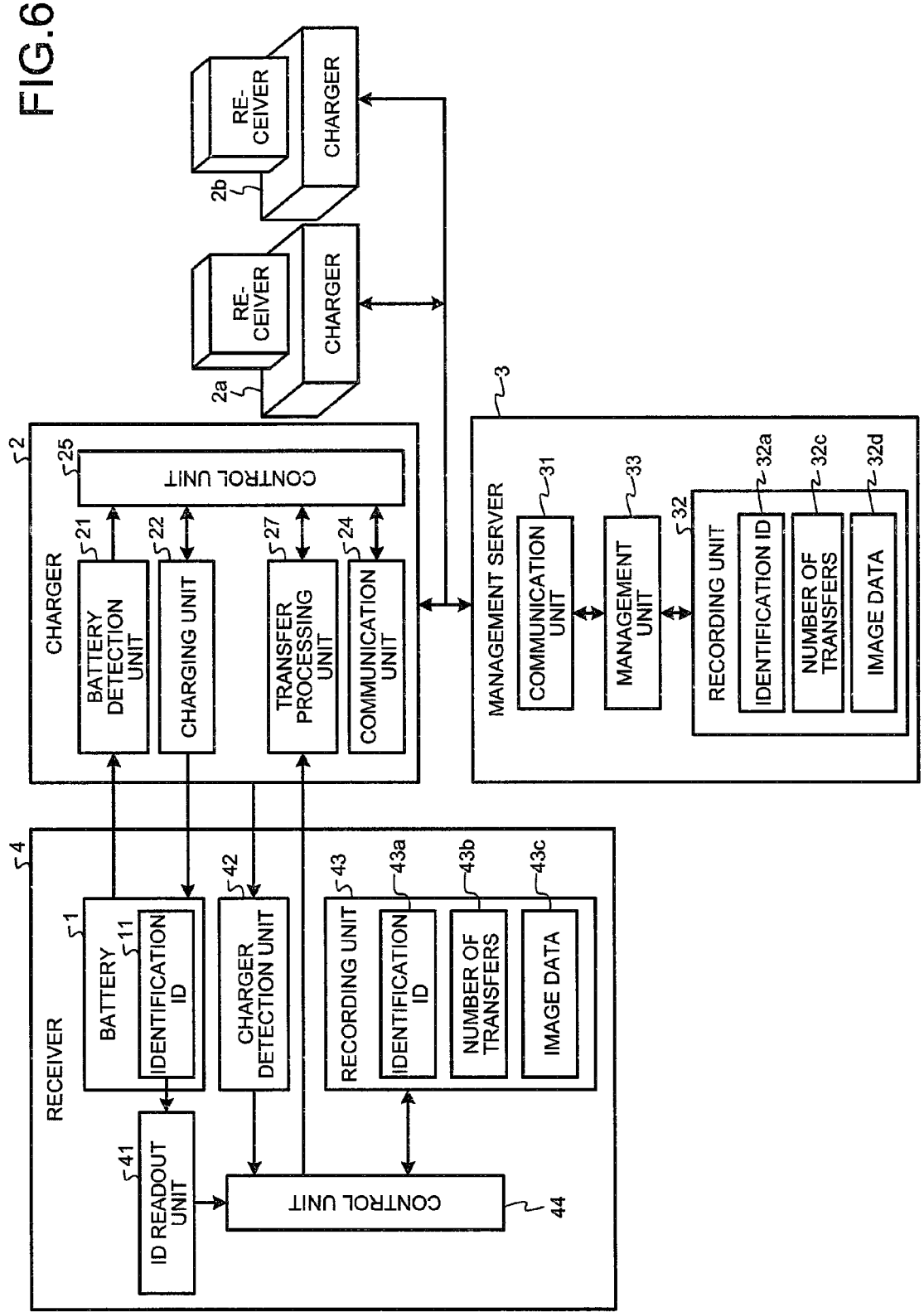
FIG. 6 is a system block diagram illustrating the configuration of a battery management system according to a third embodiment of the present invention.

FIG. 6 is a system block diagram illustrating the configuration of a battery management system according to a third embodiment of the present invention. In FIG. 6, the system is different from the battery management system shown in FIG. 4 in that the battery 1 is loaded in a receiver 4 serving as the processing device. For example, the receiver 4 includes a recording unit 43 for receiving image data from a capsule-type endoscope (not shown) for capturing images inside the subject body and recording received image data 43c. A control unit 44 detects the number of times of transfers (the number of times of processing) of image data performed by the charger 2 in the transfer processing step. The control unit 44 then cumulatively sums the detected number of times of transfers and associates it with an identification ID 43a to allow it to be recorded in the recording unit 43.

Note that the capsule-type endoscope has typically a predetermined subject image pick-up duration and pick-up rate, so that these conditions determine the amount of image data to be received by the receiver 4. This makes it possible to recognize the amount of battery consumption to be used for one transfer of image data recorded in the receiver 4. Thus, the number of times of transfers of image data by using this battery can be detected, thereby managing battery service life.

Furthermore, in the third embodiment, the receiver 4 includes an ID readout unit 41 and a charger detection unit 42. Under the control of the control unit 44, the charger detection unit 42 detects the charger 2 when it has been mounted on the charger 2 for a certain period of time and informs of the detection to the control unit 44. Under the control of the control unit 44, the ID readout unit 41 reads the identification ID attached to the battery 1 and sends the read identification ID to the control unit 44. The control unit 44 allows the aforementioned number of times of transfers corresponding to the identification ID to be recorded in the recording unit 43.

Furthermore, in the third embodiment, the charger 2 includes a transfer processing unit 27. When the receiver 4 is mounted and charging is completed, the transfer processing unit 27 performs transfer processing on the image data recorded in the recording unit 43 of the receiver 4. At this time, the transfer processing unit 27 associates the number of times of transfers 43*b* recorded in the recording unit 43 with the identification ID 43*a* and sends it as an attachment to the packet header of the image data.

Furthermore, in the third embodiment, under the control of the management unit 33, the management server 3 cumulatively sums the received number of times of transfers for each identification ID, and associates this cumulatively summed number of times of transfers 32*c* with the identification ID 32*a* to allow it to be recorded in the recording unit 32. Furthermore, received image data 32*d* can be also recorded in the recording unit 32.

Figure 7:
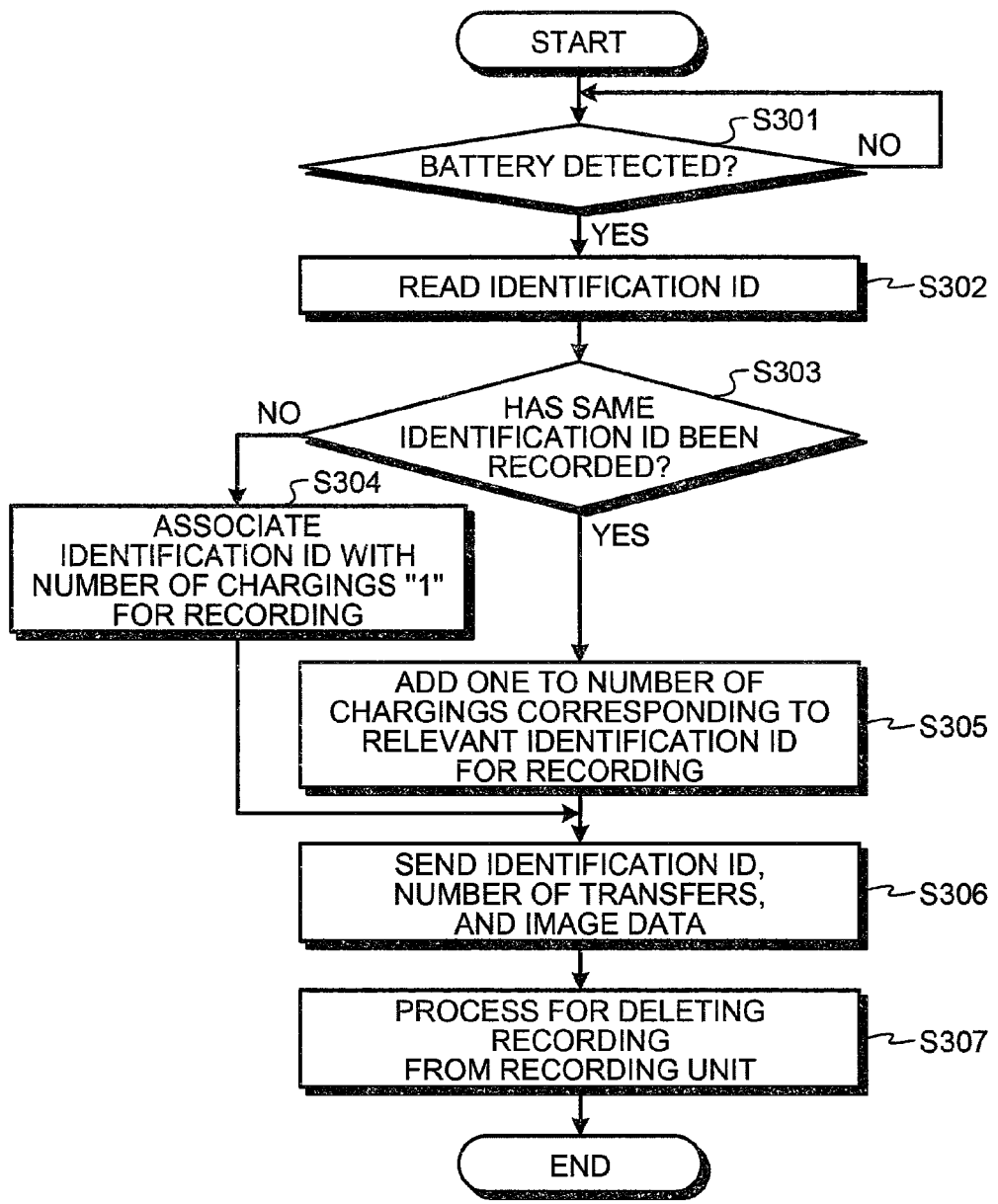
FIG. 7 is an explanatory flowchart for the control operation of a receiver shown in FIG. 6.

A description will now be made to the control operation of the receiver 4, the charger 2, and the management server 3 with reference to the flowcharts of FIGS. 7 to 9. FIG. 7 is an explanatory flowchart for the control operation of the receiver 4 shown in FIG. 6. In FIG. 7, first, if the process detects that the charger detection unit 42 has been mounted to the charger (for Yes in step S301), the control unit 44 of the receiver 4 reads the identification ID 11 attached to the battery 1 (step S302), and then searches the recording unit 43 to determine whether the same identification ID as the identification ID 11 has been recorded (step S303). Note that if the process detects that the charger detection unit 42 has not been mounted on the charger (for No in step S301), and then the control unit 44 repeats this step S301.

Here, if the same identification ID has not been recorded in the recording unit 43 (for No in step S303), then the control unit 44 associates the identification ID 11 with the number of times of transfers "1" and allows it to be temporally recorded in the recording unit 43 (step S304). If the same identification ID has been recorded (for Yes in step S303), then the control unit 44 cumulatively adds "1" to the number of times of transfers corresponding to the relevant identification ID 11 in the recording unit 43 and allows it to be temporally recorded in the recording unit 43 (step S305).

Subsequently, based on a delivery instruction from the transfer processing unit 27, the control unit 44 reads the identification ID 43*a*, the number of times of transfers 43*b*, and the image data 43*c* from the recording unit 43, and delivers them to the transfer processing unit 27 (step S306). Furthermore, the control unit 44 erases the recording of the delivered number of times of transfers 43*b* from the recording unit 43 (step S307), and then ends the aforementioned control operation.

Figure 8:
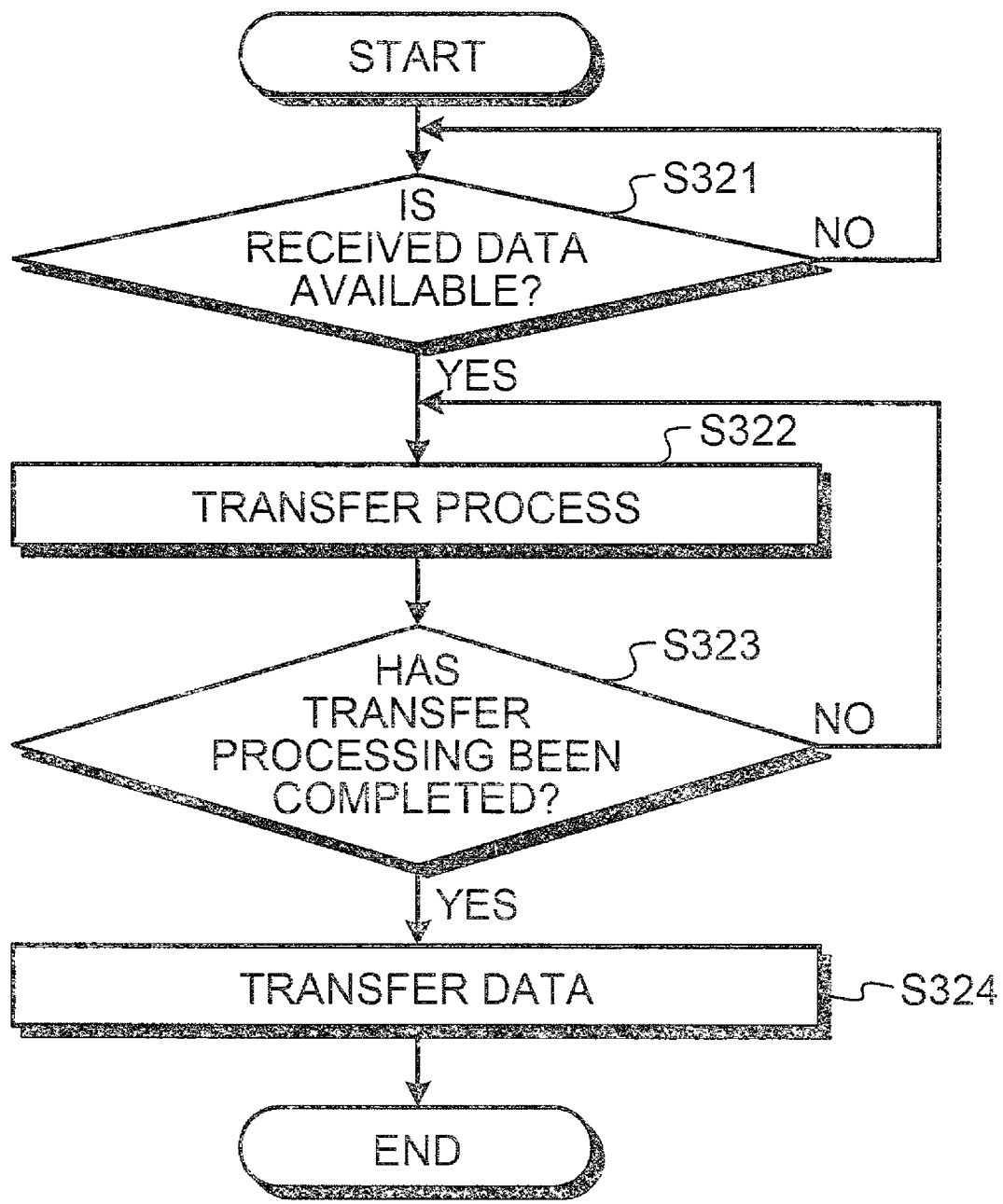
FIG. 8 is an explanatory flowchart for the transfer operation of a charger shown in FIG. 6.

FIG. 8 is an explanatory flowchart for the transfer operation of the charger 2 shown in FIG. 6. In FIG. 8, if any received image data exists in the receiver 4 (for Yes in step S321), the transfer processing unit 27 of the charger 2 acquires the identification ID 43*a*, the number of times of transfers 43*b*, and the image data 43*c* from the receiver 4, and then performs the transfer processing to create an image data packet with an image data packet header attached with the number of times of transfers associated with the identification ID (step S322). Note that during this transfer processing the control unit 25 performs the charging processing on the battery 1. On the other hand, if no received image data is available in the receiver 4 (for No in step S321), the transfer processing unit 27 repeats this step S321.

Subsequently, the transfer processing unit 27 determines whether the transfer processing has been terminated (step S323). If the transfer processing has not been terminated (for No in step S323), the process returns to step S322 to perform the transfer processing. Furthermore, if the transfer processing has been terminated (for Yes in step S323), the transfer processing unit 27 enables transferring of data to the management server via the control unit 25 and the communication unit 24 (step S324), and then ends the aforementioned transfer operation.

FIG. 9 is an explanatory flowchart for the control operation of the management server 3 shown in FIG. 6. In FIG. 9, upon reception of the image data from the charger 2 (for Yes in step S341), the management unit 33 of the management server 3 extracts the number of times of transfers associated with the identification ID 11 from the image data packet header (step S342), and then searches the recording unit 32 to determine whether the same identification ID as the identification ID 11 has been recorded (step S343). Note that if no image data has been received from the charger 2 (for No in step S341), the management unit 33 repeats this step S341.

Here, if the same identification ID has not been recorded in the recording unit 32 (for No in step S343), the management unit 33 associates the received identification ID 11 with the number of times of transfers and allows it to be recorded in the recording unit 32 (step S344). On the other hand, if the same identification ID has been recorded (for Yes in step S343), then the management unit 33 adds the number of times of transfers extracted from the packet header to the number of times of transfers corresponding to the relevant identification ID 11 in the recording unit 32 and allows it to be recorded in the recording unit 32 (step S345). Furthermore, the management unit 33 allows the received image data to be recorded in the recording unit 32 (step S346).

Subsequently, the management unit 33 determines whether the number of times of transfers corresponding to the identification ID 11 has reached the predetermined number of times (step S347). If the number of times of transfers has not yet reached the predetermined number of times (for No in step S347), then the process determines that the battery 1 has not yet reached its useful life limit and is still usable in the normal condition (step S348). On the other hand, if the number of times of transfers has reached the predetermined number of times (for Yes in step S347), then the process determines that the battery 1 has reached its useful life limit and has to be replaced (step S349). Upon completion of the aforementioned determinations, the management unit 33 outputs the determination result to the charger 2 (step S350), and then ends the aforementioned control operation.

As such, in the third embodiment, in place of the number of chargings, the number of times of transfers by the charger is associated with the identification ID and sent to the management server 3. When the management server 3 receives the number of times of transfers from each of the chargers 2, 2*a*, and 2*b*, the management server 3 cumulatively sums the number of times of transfers for each identification ID, associates this cumulatively summed number of times of transfers with the identification ID and allows it to be recorded. In addition to this, the management server 3 manages battery service life based on the number of times of transfers. It is thus possible for the management server to provide simple centralized management of the service life of batteries as with the second embodiment.

Furthermore, in the third embodiment, the data regarding the number of times of transfers is temporarily recorded in the image data recording unit 43 that is typically available to the receiver 4. This makes it possible to record the number of times of transfers without the need of an additional database, thereby preventing increases in parts counts and manufacturing costs.

Furthermore, in the third embodiment, the number of times of transfers is attached to the packet header of image data and transferred to the management server 3, thereby making it possible to transfer the number of times of transfers to the management server 3 without any increase in transmission traffic.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A battery management system comprising:
a plurality of receivers, each comprising a corresponding battery, wherein the corresponding battery is loaded into each of the plurality of receivers and each corresponding battery comprises an identification ID attached thereto, wherein each of the plurality of receivers is configured for reading the identification ID attached to the corresponding battery;
a plurality of chargers configured for charging the battery to which the plurality of receivers are respectively mounted; and
a management server connected to each of the chargers and configured for receiving information sent from each of the chargers;
wherein:
the receiver is configured for:
detecting a number of times of transfers of the image data by the charger;
recording received image data;
associating a receiver identification ID with the detected number of times of transfers; and
allowing the detected number of times of transfer of the image data to be recorded corresponding to the receiver identification ID;
the plurality of chargers are configured for:
acquiring the receiver identification ID, the number of times of transfers, and the image data recorded in the receiver; and
sending the image data together with the number of the transfers of the image data associated with the receiver identification ID; and
the management server is configured for:
receiving information sent from each of the chargers regarding the number of times of transfers of the image data associated with the receiver identification ID;
cumulatively summing the received number of times of transfer of the image data for each receiver identification ID;
associating the receiver identification ID with the cumulatively summed number of chargings and allowing the number of chargings to be recorded; and
determining that the corresponding battery has reached its useful life limit when the cumulatively summed number of transfers has reached a predetermined number.

2. The battery management system according to claim 1, wherein the charger is configured to create an image data packet comprising the image data and a packet header comprising the number of times of transfer associated with the receiver identification ID.

3. The battery management system according to claim 1, wherein the charger is configured to erase from the receiver the number of times of transfer that is acquired by the charger.

4. The battery management system according to claim 3, wherein
the battery attached with the identification ID is loaded in a processing device for performing predetermined processing;
in place of the number of chargings of the battery, the charger associates the identification ID with the number of times of processing performed by the processing device and sends the number of times of processing; and
the management server receives the number of times of processing associated with the identification ID and sent from each of the chargers, the management server cumulatively summing the number of times of processing for each identification ID, the management server associating the identification ID with the cumulatively summed number of times of processing and allowing the number of times of processing to be recorded, the management server managing battery service life based on the number of times of processing.

* * * * *